(12) United States Patent
Sakabe et al.

(10) Patent No.: US 10,701,788 B2
(45) Date of Patent: Jun. 30, 2020

(54) POWER UNIT AND MEDICAL ELECTRIC DEVICE

(71) Applicants: FUJIKIN INCORPORATED, Osaka (JP); T&S CORPORATION, Chiba (JP)

(72) Inventors: Toshiro Sakabe, Osaka (JP); Toyohiko Aoki, Chiba (JP); Kiyomi Watanabe, Chiba (JP); Shin Yokoshima, Chiba (JP)

(73) Assignees: FUJIKIN INCORPORATED, Osaka (JP); T&S CORPORATION, Shiba (JP)

( * ) Notice: Subject to any disclaimer, the term of this patent is extended or adjusted under 35 U.S.C. 154(b) by 7 days.

(21) Appl. No.: 16/226,929

(22) Filed: Dec. 20, 2018

(65) Prior Publication Data

US 2019/0200440 A1   Jun. 27, 2019

(30) Foreign Application Priority Data

Dec. 27, 2017   (JP) ................. 2017-251372

(51) Int. Cl.
| | |
|---|---|
| *H05G 1/12* | (2006.01) |
| *A61B 6/00* | (2006.01) |
| *H02M 7/5387* | (2007.01) |
| *H03K 17/78* | (2006.01) |
| *H02M 7/04* | (2006.01) |

(52) U.S. Cl.
CPC ............ *H05G 1/12* (2013.01); *A61B 6/40* (2013.01); *A61B 6/54* (2013.01); *A61B 6/56* (2013.01); *H02M 7/5387* (2013.01); *H02M 7/04* (2013.01); *H03K 17/78* (2013.01)

(58) Field of Classification Search
CPC .... H05G 1/12; A61B 6/40; A61B 6/54; A61B 6/56; H02M 7/5387; H02M 7/04; H03K 17/78
See application file for complete search history.

(56) References Cited

PUBLICATIONS

International Electrotechnical Commission; IEC 60601-1, Edition 3.1, Aug. 2012.
NKK Switches for Medical Electrical Equipment; Technical Reference, Apr. 2016, p. 5.

*Primary Examiner* — Robert L Deberadinis
(74) *Attorney, Agent, or Firm* — W&C IP

(57) ABSTRACT

Provided is a power unit including: a power converter circuit connected to an external power supply, the power converter circuit being configured to generate a voltage necessary to drive a driven device; a communication terminal connected to a controller, the communication terminal being configured to transmit and receive information between the controller and the driven device; a power supply control terminal connected to the controller, the power supply control terminal being applied with a direct current voltage from the controller; and a relay element provided between the external power supply and the power converter circuit, the relay element being configured to control supply of electric power to the power converter circuit, wherein the relay element is driven by a direct current voltage applied from the power supply control terminal when a power supply of the controller is turned on, and electric power is supplied to the power converter circuit.

7 Claims, 4 Drawing Sheets

POWER UNIT AND MEDICAL ELECTRIC DEVICE

BACKGROUND

Technical Field

The present invention relates to a power unit and a medical electric device, such as a radiographic imaging device, having the power unit.

Related Art

In various medical electric devices including radiographic imaging devices and X-ray image generation systems, there are known devices that conduct control on the screen of a controller, such as a computer.

Specifically, the medical electric device has a controller for manipulation. The controller is connected to a central processing unit (CPU, a so-called microcomputer) in the main body of the medical electric device through a communication cable. The controller transmits a set point signal to the medical electric device through the communication cable for control. The controller receives information of the medical electric device main body through the communication cable. A user can control the medical electric device through the display unit of the controller, and can acquire information of the medical electric device. In an X-ray irradiation device, a user can set a voltage and an electric current to be applied to an X-ray tube and irradiation time, and can monitor irradiation results through the screen of a controller.

The medical electric device, a radiographic imaging device, for example, is composed of a power converter that supplies a direct current high voltage, a filament current, and any other power to a driven device, such as an X-ray tube, i.e. the device is composed of an X-ray high voltage generator and a controller that controls the generator.

In the approval and authentication for marketing, for example, medical electric devices are required to conform to International Standard IEC 60601-1 (Medical electrical equipment—Part 1: General requirements for basic safety and essential performance). In order to conform to the standard, the power supplies of medical electric devices have to be turned on and off using mechanical switches prescribed in the standard.

However, the power supply of the radiographic imaging device is large, and disposed at a location near to the X-ray tube. Thus, a user usually manipulates the power supply at a remote site from the power unit through the controller.

As shown in FIG. 4, in a previously existing configuration, in a medical electric device main body 101, an activation-low-voltage-direct-current power supply 43 is provided. The power supply 43 is formed of a transformer 45, a rectifier 44 and any other component, and generates a low direct current voltage of approximately 24 V from an alternating power supply 3. The activation-low-voltage-direct-current power supply 43 is connected to one pole of a manipulation coil 5 of an electromagnetic switch 6. The other pole of the manipulation coil 5 is connected to a power supply switch 46 through a cable. The switch 46 is disposed on the outside of the medical electric device main body 101. The switch 46 mechanically operates.

Upon turning on the power supply switch 46, a direct current is carried from the alternating power supply 3 to the manipulation coil 5 of the electromagnetic switch 6 through the activation-low-voltage-direct-current power supply 43. This turns on the electromagnetic switch 6 to start the supply of electric power from the alternating power supply 3 to an X-ray high voltage generator 7. This configuration enables a configuration in which the power supply switch 46 can be installed at the remote location while the shortest current supply path from the alternating power supply 3 to the X-ray high voltage generator 7 is kept. However, the activation-low-voltage-direct-current power supply 43 is always on, resulting in a large standby power.

Note that the electromagnetic switch 46 can be operated using the alternating power supply as it is with no use of the activation-low-voltage-direct-current power supply 43. However, routing a high alternating power supply voltage to the power supply switch 46 that the user manipulates is not conducted because of safety.

In the case in which the medical electric device main body 1 is activated, the mechanical power supply switch 46 of the medical electric device and a mechanical power supply switch 27 of a controller 2 have to be separately turned on, resulting in complicated manipulation.

SUMMARY

An aspect of the present invention is to supply electric power to a medical electric device with less manipulation. Another aspect of present invention is to omit a power supply box dedicated to a power supply switch with functions kept, and the number of components is reduced.

In order to achieve the objects, in the aspects, attention is focused on the facts that most of controllers, e.g. personal computers, always use a mechanical switch for the switch to turn on the power supply of the personal computer and that in the Universal Serial Bus (USB) standard, the USB port of the personal computer outputs a direct current voltage of five volts for external supply and a direct current voltage of approximately 500 mA in synchronization of turning on the power supply of the personal computer, separately from the signal system.

In order to achieve the objects, according to an aspect of the present invention, there is provided a power unit including: a power converter circuit connected to an external power supply, the power converter circuit being configured to generate a voltage necessary to drive a driven device; a communication terminal connected to a controller, the communication terminal being configured to transmit and receive information between the controller and the driven device; a power supply control terminal connected to the controller, the power supply control terminal being applied with a direct current voltage from the controller; and a relay element provided between the external power supply and the power converter circuit, the relay element being configured to control supply of electric power to the power converter circuit, wherein the relay element is driven by a direct current voltage applied from the power supply control terminal when a power supply of the controller is turned on, and electric power is supplied to the power converter circuit.

The power supply control terminal may be composed of one terminal, and the communication terminal may be composed of one terminal, and the power supply control terminal and the communication terminal may be connectable to a terminal of the controller.

The relay element may be an optically isolated relay having a light emitting element, and the light emitting element may be connected to the power supply control terminal.

The relay element may be an electromagnetic switch, and a manipulation coil of the electromagnetic switch may be connected to the power supply control terminal.

The controller may have a power supply switch that mechanically operates, upon turning on the power supply of the controller by the power supply switch, the controller may supply a direct current voltage to the power supply control terminal to start supply of electric power to the power converter circuit.

The power unit may further include a cable connecting the relay element to the controller, the cable may have a switch that mechanically operates, and the switch may switch whether to transfer the direct current voltage from the controller to the relay element.

Furthermore, according to another aspect of the present invention, there is provided a medical electric device including: a power converter circuit configured to supply a high voltage to a driven device; a controller connected to the power converter circuit, the controller being configured to control operation of the driven device; and a power unit connected to the power converter circuit, the power supply being configured to supply electric power to the power converter circuit, wherein the power unit is any of the power units described above.

According to the aspects of the present invention, a cabled controller dedicated to the power supply switch is eliminated, and hence the number of components can be reduced. No activation direct current power supply is provided, and hence standby power can be reduced. Electric power can be supplied to the medical electric device main body with less manipulation.

Conventionally, which one of the medical electric device main body and the controller is first activated depends on a user. Thus, the activation sequence of the medical electric device is complicated because the sequence is designed to cope with activation of both of the main body and the controller. In the aspects of the present invention, the controller is guaranteed to be always turned on prior to the medical electric device main body. Thus, the design of the activation sequence of the medical electric device is made simple.

DETAILED DESCRIPTION

Medical Electric Device 1

In the following, as an example of a medical electric device according to an exemplary embodiment of the present invention, an embodiment of an X-ray irradiation device will be described with reference to the drawings.

Figure 1:
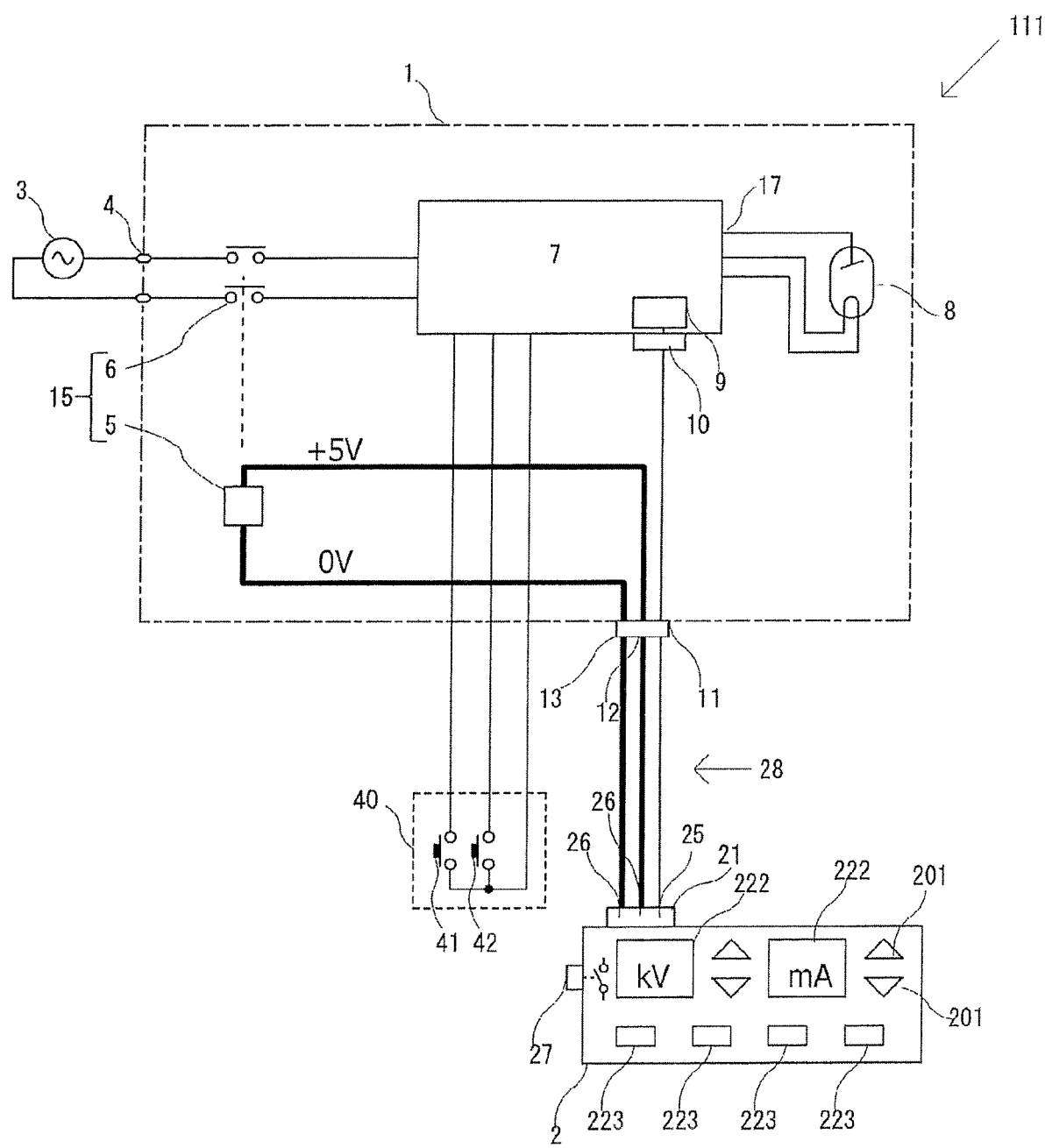
FIG. 1 is a circuit block diagram of a first embodiment of a medical electric device according to an exemplary embodiment of the present invention.

FIG. 1 shows a first embodiment of the present invention. A medical electric device 111 is a radiographic imaging device, for example, mainly formed of a medical electric device main body 1 and a controller 2 that manipulates the medical electric device main body 1.

The medical electric device main body 1 has a receiving terminal 4, an X-ray high voltage generator 7, an X-ray tube 8, a relay element 15, and a communication-and-power-supply control connector 11. The receiving terminal 4 is a terminal connected to an external alternating power supply 3. The medical electric device main body 1 receives an electric current from the external alternating power supply 3 through the receiving terminal 4, and conducts the current to an electromagnetic switch 6 of the relay element 15. The alternating power supply 3 is connected to the X-ray high voltage generator 7 through the electromagnetic switch 6. The X-ray high voltage generator 7 has an output end 17 connected to the X-ray tube 8. The X-ray high voltage generator 7 is an example of a power converter circuit. The X-ray tube 8 is an example of a driven device.

The X-ray high voltage generator 7 is controlled by an internal information processing unit 9. The information processing unit 9 is composed of a CPU, a random access memory, and a communication processing circuit. The information processing unit 9 has a communication terminal 10. The communication terminal 10 is connectable to the controller 2 disposed on the outside of the medical electric device main body 1.

The communication-and-power-supply control connector 11 is a connector integrally composed of the communication terminal 10 and power supply control terminals 12 and 13. Both ends of a manipulation coil 5 of the electromagnetic switch 6 are respectively connected to the power supply control terminals 12 and 13.

The X-ray high voltage generator 7, the communication terminal 10, the power supply control terminal 12 to 13, and the relay element 15 constitute a power unit. In the embodiment, the power unit is built in the medical electric device main body 1 that is one of the components of the medical electric device 111. The power supply generates a predetermined voltage in response to turning on the power supply of the controller 2 to drive the driven device 8. Note that a configuration may be provided in which the power unit is disposed on the outside of the X-ray high voltage generator 7 and connected to the X-ray high voltage generator 7 through an appropriate component.

The X-ray high voltage generator 7 generates electric power necessary to drive the X-ray tube 8. The X-ray high voltage generator 7 includes, for example, a plurality of semiconductor switching devices that constitutes a switching regulator, a full bridge circuit, or a half bridge circuit, a transformer, a rectifier, the information processing unit 9 that controls voltages and conducts inputs and outputs to the outside, and any other component. The X-ray high voltage generator 7 converts an alternating current supplied from the alternating power supply 3 into a direct current using the rectifier, and generates an alternating current voltage using an inverter formed of an insulated-gate bipolar transistor bridge circuit. The transformer boosts the alternating current voltage, the rectifier rectifies the voltage boosted by the transformer, and hence the X-ray high voltage generator 7 generates a predetermined direct current high voltage. The alternating power supply 3 is a 200-volt commercial power supply, for example. The voltage on the secondary winding of the transformer ranges from approximately 40 to 150 kV, for example. However, the voltage of the transformer is non-limiting. The transformer may be a transformer that outputs a voltage ranging from approximately 200 to 400 kV or higher. The high voltage is supplied to the X-ray tube 8 at necessary timing.

The communication terminal 10 is a terminal that transmits and receives signals between the controller 2 and the medical electric device main body 1. Signals inputted and outputted through a controller connector 21 of the controller 2 are processed at the information processing unit 9 and any other component, and the controller 2 can manipulate the medical electric device main body 1 and acquire measurement data using the signals.

The communication-and-power-supply control connector 11 is a terminal connected to the controller connector 21 of the controller 2 through a cable, and to the connector 11, a direct current voltage is applicable from the controller connector 21 to the connector 11.

The communication-and-power-supply control connector 11 has two power supply control terminals 12 and 13. The voltage across the power supply control terminals 12 and 13 is five volts, for example. These two power supply control terminals 12 and 13 are connected to the manipulation coil 5 in the inside of the medical electric device main body 1.

The communication-and-power-supply control connector 11 is connected to the controller connector 21 composed of one USB port, for example, included in the controller 2. That is, a direct current voltage from the controller 2 is applied to the power supply control terminals 12 and 13 through the USB port. The configuration in which the communication-and-power-supply control connector 11 includes one USB port enables a reduction in the number of components and in the number of cables.

Note that the communication-and-power-supply control connector 11 only has to be a connector having a power supply terminal. The connector 11 may be an IEEE 1394 connector, for example. A cable in this case is an IEEE 1394 cable.

Note that the communication terminal 10 of the information processing unit 9 may be a Bluetooth (registered trademark) transmitter-receiver instead of a physical connection terminal. In this case, the controller 2 also has a transmitter-receiver that can communicate with the communication terminal 10 in a wireless manner, and can transmit and receive information through the transmitter and the receiver.

The relay element 15 is an optically isolated relay using a solid-state relay or a photo relay, for example. The optically isolated relay is a relay using a light emitting diode on the input side and a semiconductor device, such as a photo triac/phototransistor/photothyristor device, on the output side. A photo triac/photothyristor device is limited to an alternating load.

The photo relay is a photocoupler composed of a light emitting diode on the input side and a metal oxide silicon field effect transistor on the output side. The photo relay is superior to a mechanical relay on long lifetime, low electric current drive, and high-speed responses.

The relay element 15 may be composed of a light emitting diode that is a light emitting element and a phototransistor that is a light receiving device. The input end of the relay element 15 is connected to the power supply control terminal 12. The output end of the relay element 15 controls the connection of the X-ray high voltage generator 7 to the alternating power supply 3.

The relay element 15 may be an electromagnetic switch instead of the relay element 15. The electromagnetic switch has a similar wiring. In the case in which the USB power supply port can supply electric power enough to directly drive the electromagnetic switch 6, the electromagnetic switch 6 is turned on and off using power fed from the controller 2 through the USB port, and this enables the control of connection of the X-ray high voltage generator 7 to the alternating power supply 3.

A power feed terminal 26 is a terminal connected to the medical electric device main body 1 through a cable, for example. The power feed terminal 26 feeds power from the controller connector 21 to the relay element 15. A communication cable 28 transmits information from the X-ray high voltage generator 7 and the peripheral devices of the generator 7, e.g. the X-ray tube and a collimator, to the controller 2. The medical electric device main body 1 receives instructions from the controller 2 through the communication-and-power-supply control connector 11 for various operations of control.

The controller 2 is a computer, for example. Specifically, the controller 2 may be a general-purpose personal computer. The controller 2 may be a computer specifically configured for medical electric devices.

The controller 2 includes a transmission unit and a manipulation unit, not shown, and the controller connector 21, and the power supply switch 27.

The transmission unit transmits information received from the X-ray high voltage generator 7 through the controller connector 21. Specifically, the transmission unit includes various components, such as a display unit, i.e. a screen, and a speaker.

On the screen of the controller 2, up-down buttons 201 that increase or decrease the set values of the X-ray tube voltage (kV) and the X-ray tube current (mA), indicators 222 that indicate the set values, and part buttons 223 for anatomic programming (APR), for example, are displayed.

The manipulation unit generates instructions to the X-ray high voltage generator 7 by user manipulation. Specifically, the manipulation unit includes various components, such as a keyboard and a mouse. In the case in which the computer is a tablet, the manipulation unit may be a touch panel with no keyboard nor mouse.

The controller connector 21 is a terminal connected to the communication-and-power-supply control connector 11. The controller connector 21 is a USB port, for example, used for supplying an electric current from the controller 2 to the outside.

The controller connector 21 has a controller communication terminal 25 that transmits and receives manipulation information and measurement information to and from the communication terminal 10 of the X-ray irradiation device. Communication signals from the controller communication terminal 25 are serially converted, and connected to the communication terminal 10 of the information processing unit 9 through the communication-and-power-supply control connector 11.

The controller connector 21 has the power feed terminal 26 for external supply. The power feed terminal is connected to the manipulation coil 5 through the power supply control terminals 12 and 13 of the communication-and-power-supply control connector 11. The power supplied from the power feed terminal 26 is a direct current voltage of five volts, for example.

The power supply switch 27 is a mechanical switch that is a push button switch or a change-over switch, for example. The user manipulates the power supply switch 27 to switch between turning on and off the power supply of the controller 2.

The X-ray high voltage generator 7 is connected to a hand switch 40. The hand switch 40 is a switch that controls the current-carrying state from the X-ray high voltage generator 7 to the X-ray tube 8 when electric power is supplied from the alternating power supply 3 to the X-ray high voltage generator 7. The hand switch 40 has a first switch 41 and a second switch 42 connected to different places in the X-ray high voltage generator 7. The first and the second switches 41 and 42 are switches that the user can physically manipulate. The switches 41 and 42 are a push button switch or a change-over switch, for example.

The controller 2 is configured such that upon turning on the power supply switch 27, the power supply of the controller 2 is turned on, and a direct current voltage is applied to the power feed terminal 26. The voltage applied to the power feed terminal 26 is supplied to the power supply control terminals 12 and 13 of the medical electric device main body 1 through the cable connected to the power feed terminal 26. Upon application of the voltage to the power supply control terminals 12 and 13, an electric current enough to turn on the relay element 15 is carried. Upon turning on the relay element 15, the supply of electric power is started from the alternating power supply 3 to the X-ray high voltage generator 7 to activate a control microcomputer or charge a power supply capacitor, and the state is transitioned to an operation preparation state in which the X-ray irradiation device is ready to start X-ray irradiation from the X-ray tube 8. After manipulation is made with the hand switch 40 in the operation preparation state, an electric current is carried through the filament of the X-ray tube 8 by manipulation of the first switch 41, and X-rays are irradiated by manipulation of the second switch 42.

Upon turning off the power supply switch 27 of the controller 2 to turn off the power supply of the controller 2, no voltage is applied to the power feed terminal 26, and hence the electric current carried through the relay element 15 is turned off. Consequently, the relay element 15 is turned off, and the alternating power supply 3 stops the supply of electric power to the X-ray high voltage generator 7. Similarly in the case in which the cable connecting the power supply control terminals 12 and 13 to the power feed terminal 26 is disconnected, the relay element 15 is automatically turned off, and the supply of electric power to the X-ray high voltage generator 7 is stopped.

As described above, in accordance with the embodiment of the medical electric device according to the exemplary embodiment of the present invention, the power supply switch 27 of the controller 2 is turned on, and hence the supply of electric power from the alternating power supply 3 to the X-ray high voltage generator 7 can be started. Consequently, compared with the previously existing configuration in which the medical electric device main body 1 and the power supply of the controller 2 are activated by separate manipulations, electric power can be applied to the medical electric device with less manipulation. With this configuration, the medical electric device main body 1 and the controller 2 share the power supply switch, and hence there is no need to dispose a power supply switch that mechanically operates the medical electric device main body 1. Consequently, compared with the previously existing configuration, the medical electric device can be configured with a small number of components.

In accordance with the embodiment of the medical electric device according to the exemplary embodiment of the present invention, in the case in which the cable connecting the communication-and-power-supply control connector 11 to the controller connector 21 of the controller 2 is disconnected, the supply of electric power to the medical electric device is stopped. Accordingly, even in the case in which connection through the cable is disconnected due to an eventuality, the medical electric device can be stopped in an emergency. Conventionally, the power supply switch of the medical electric device and the power supply switch of the controller 2 are separately provided, the user usually is near the controller 2, and hence the user has to quickly move to the power supply switch in the case of an emergency stop. On the contrary, in accordance with the medical electric device according to the embodiment of the present invention, the medical electric device can be turned off while the user is near the controller 2.

In accordance with the embodiment of the medical electric device according to the exemplary embodiment of the present invention, there is no need to provide the mechanical switch on the medical electric device main body 1, and hence the medical electric device main body 1 can be downsized. Therefore, the power unit according to the embodiment of the present invention is useful also in the case in which the power unit is applied to a portable X-ray irradiation device.

In accordance with the embodiment of the medical electric device according to the exemplary embodiment of the present invention, when no power is fed to the X-ray irradiation device, the alternating power supply 3 is electrically interrupted from the X-ray high voltage generator 7 using the relay element 15, and hence standby power can be nearly zero.

Medical Electric Device 2

A second embodiment of the medical electric device according to the exemplary embodiment of the present invention will be described mainly on differences from the embodiment described above. The embodiment is different from the first embodiment described above that a second relay element controls continuity between an alternating power supply and an activation auxiliary power supply in the case in which an electric current supplied through the USB port of a controller 2 is not enough to directly drive a manipulation coil of an electromagnetic switch. Note that in the following description, components similar to the components of the first embodiment are designated with the same reference signs.

Figure 2:
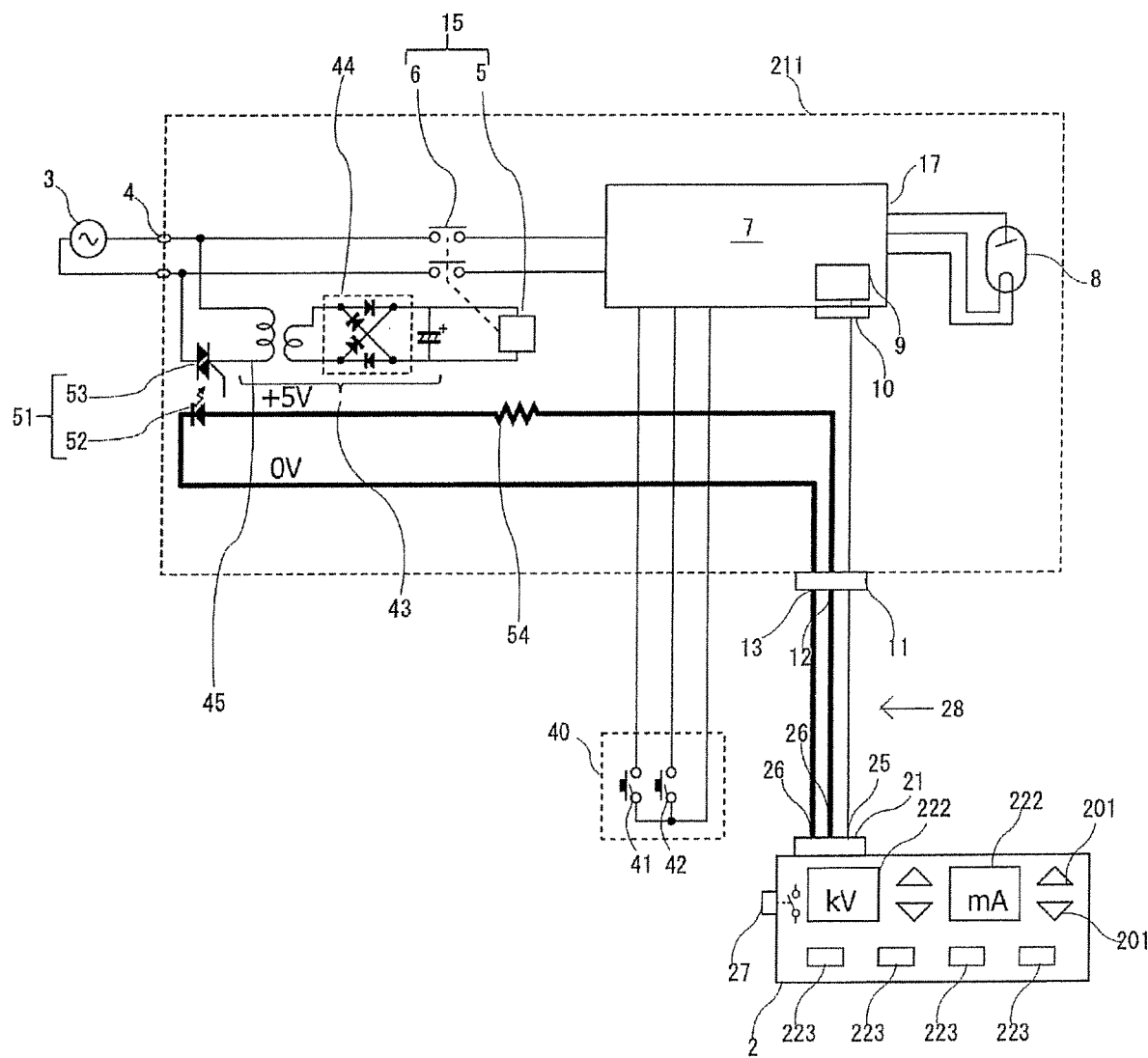
FIG. 2 is a circuit block diagram of a second embodiment of a medical electric device according to an exemplary embodiment of the present invention.

As shown in FIG. 2, a medical electric device main body 211 includes an electromagnetic switch 6 of a power circuit having a manipulation coil 5 and a photo triac 51 that is a second relay element inserted into the input of an activation auxiliary power supply.

The photo triac 51 is composed of a light emitting diode 52 and a photo triac 53. Note that the second relay element 51 may be an electromagnetic switch similar to the first relay element. However, the drive current of the manipulation coil 5 has to be smaller than the electric current that can be supplied through a USB port.

The light emitting diode 52 is connected to power supply control terminals 12 and 13. Note that, the light emitting diode 52 is desirably connected to a current limiting resistor 54 in series.

The photo triac 51 controls the continuity between an alternating power supply 3 and the input of an activation-low-voltage-direct-current power supply 43. After a power supply switch 27 is pushed to activate the controller 2 for application of a direct current voltage applied to the power supply control terminals 12 and 13, the light emitting diode 52 is turned on, and the photo triac 51 is turned on. A direct current enough to turn on the manipulation coil 5 is carried via an activation direct current power supply transformer 45 and a rectifier 44. Upon turning on the electromagnetic switch 6, the supply of electric power from the alternating power supply 3 to an X-ray high voltage generator 7 is started, and the state is transitioned to the operation preparation state.

According to the medical electric device 211 as shown in FIG. 2, even in the case in which electric power supplied from the controller 2 to the power supply control terminal 12 is short and this causes a failure to directly drive the manipulation coil 5 of the electromagnetic switch 6 because of a large coil voltage and a large coil current, the electromagnetic switch 6 can be driven through the relay element 51 in a smaller size.

Medical Electric Device 3

A third embodiment of the medical electric device according to the exemplary embodiment of the present invention will be described on the differences from the embodiments described above. The embodiment is different from the embodiments described above that a switch is provided in series on a cable connecting the power supply control terminal of a medical electric device main body to a controller. Note that in the following description, components similar to the components of the first embodiment are designated with the same reference signs.

Figure 3:
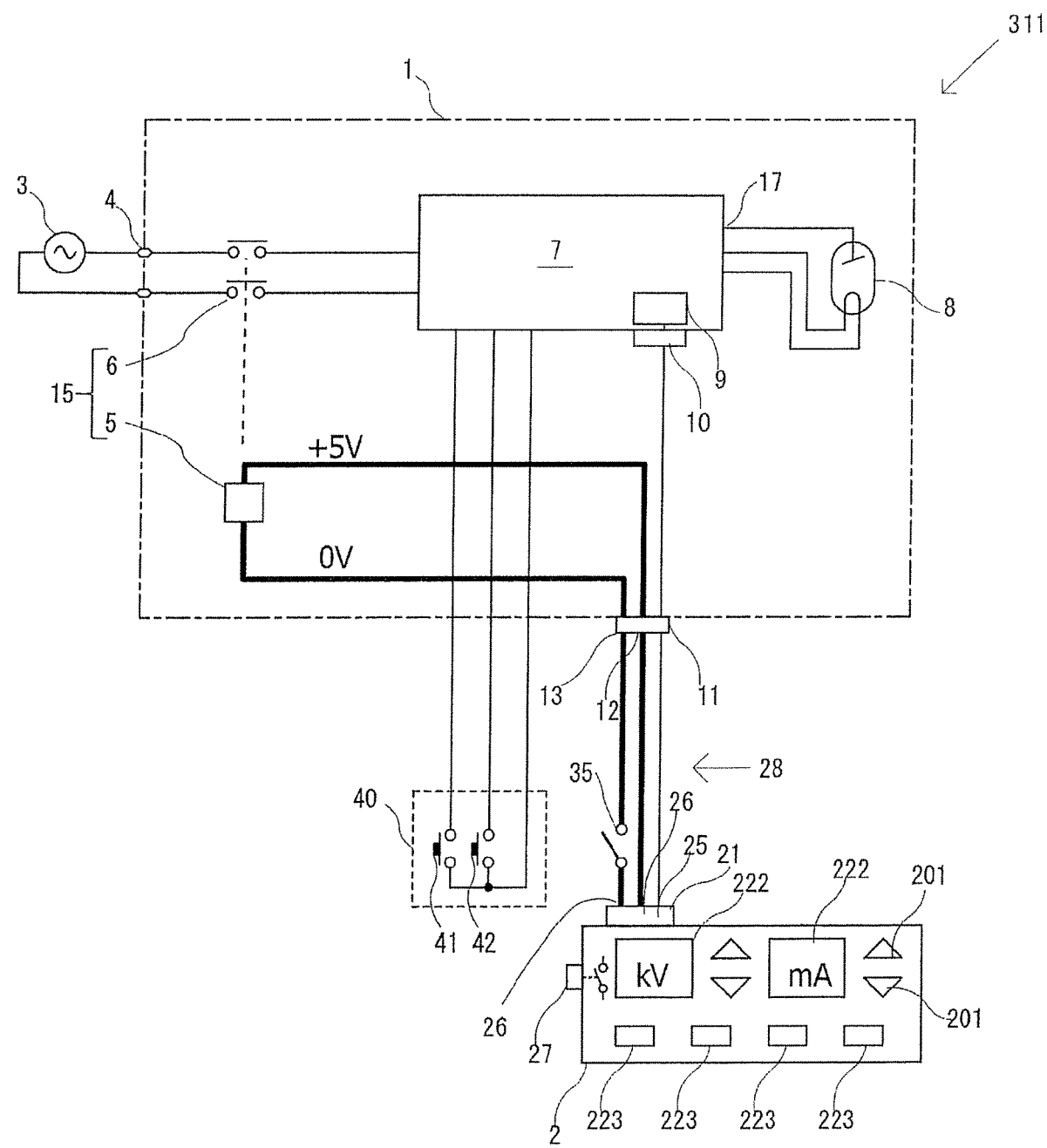
FIG. 3 is a circuit block diagram of a third embodiment of a medical electric device according to an exemplary embodiment of the present invention.
Figure 4:
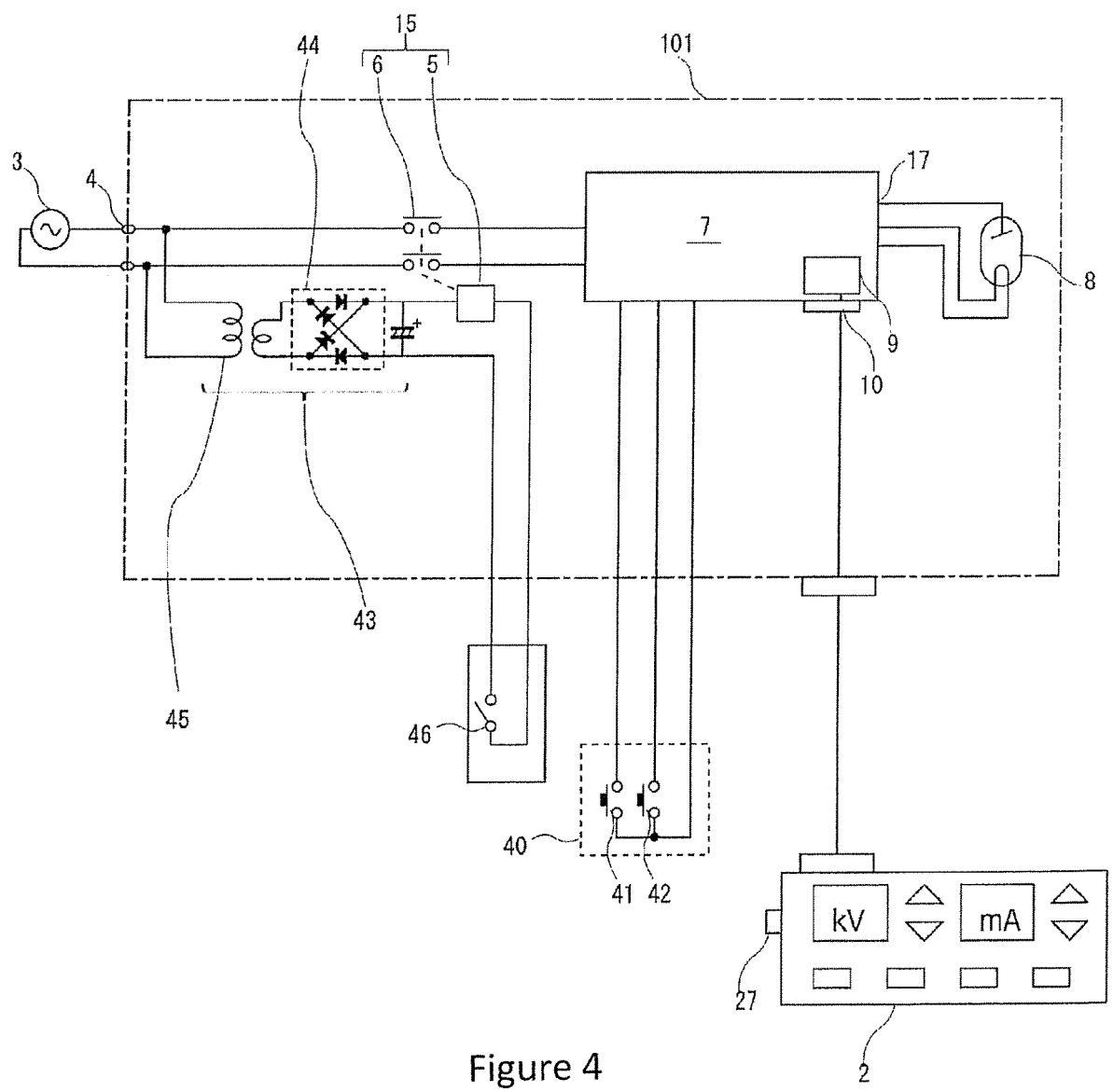
FIG. 4 is a circuit block diagram of a previously existing medical electric device.

As shown in FIG. 3, in a medical electric device 311, a switch 35 is provided in series on a cable connecting a controller 2 to a medical electric device main body 1. The switch 35 is a mechanical switch that is a push button switch or a change-over switch, for example. The switch 35 is provided near the connecting part to the controller 2, for example, at a position at which an operator of the controller 2 can immediately manipulate the switch 35. Similarly to the case of the power supply switch 27, turning on and off the switch 35 switches the power feed state to a power feed terminal 26, and hence turning on and off the power supply of the medical electric device main body 1 can be manipulated.

According to the third embodiment of the medical electric device 311, for example, in the case in which a USB cable or an IEEE 1394 cable is used as a cable, the function equivalent to a previously existing cabled controller dedicated to a power supply switch can be achieved without additionally providing a new cable or a new controller. In the case in which the medical electric device 311 is usually used with the switch 35 turned on, the switch 35 can be used as an interrupter switch for an emergency stop while a switch manipulation load is reduced, similarly to the first embodiment.

In the third embodiment, the controller 2 may always supply a direct current voltage to the power feed terminal 26 regardless of the activation state. In this case, the switch 35 functions as a physical switch that turns on and off the power supply of the medical electric device 311.

In the foregoing embodiments, the X-ray irradiation device is described as a medical electric device. However, the present invention is non-limiting. The present invention is applicable to other medical electric devices and electric devices that are not intended for medical use.

What is claimed is:

1. A power unit comprising:
   a power converter circuit connected to an external power supply, the power converter circuit being configured to generate a voltage necessary to drive a driven device;
   a communication terminal connected to a controller, the communication terminal being configured to transmit and receive information between the controller and the driven device;
   a power supply control terminal connected to the controller, the power supply control terminal being applied with a direct current voltage from the controller; and
   a relay element provided between the external power supply and the power converter circuit, the relay element being configured to control supply of electric power to the power converter circuit, wherein
   the relay element is driven by a direct current voltage applied from the power supply control terminal when a power supply of the controller is turned on, and electric power is supplied to the power converter circuit.

2. The power unit according to claim 1, wherein
   the power supply control terminal is composed of one terminal, and the communication terminal is composed of one terminal, and
   the power supply control terminal and the communication terminal are connectable to a port of the controller.

3. The power unit according to claim 1, wherein
   the relay element is an optically isolated relay having a light emitting element, and
   the light emitting element is connected to the power supply control terminal.

4. The power unit according to claim 1, wherein
   the relay element is an electromagnetic switch, and
   a manipulation coil of the electromagnetic switch is connected to the power supply control terminal.

5. The power unit according to claim 1, wherein
   the controller has a power supply switch that mechanically operates,
   upon turning on the power supply of the controller by the power supply switch, the controller supplies a direct current voltage to the power supply control terminal to start supply of electric power to the power converter circuit.

6. The power unit according to claim 1, further comprising
   a cable connecting the relay element to the controller, wherein
   the cable has a switch that mechanically operates, and
   the switch switches whether to transfer the direct current voltage from the controller to the relay element.

7. A medical electric device comprising:
   a power converter circuit configured to supply a high voltage to a driven device;
   a controller connected to the power converter circuit, the controller being configured to control operation of the driven device; and
   a power unit connected to the power converter circuit, the power supply being configured to supply electric power to the power converter circuit, wherein
   the power unit is the power unit according to claim 1.

* * * * *